(12) United States Patent
Saffie-Siebert et al.

(10) Patent No.: US 9,750,697 B2
(45) Date of Patent: Sep. 5, 2017

(54) DELIVERY OF AN ACTIVE MATERIAL (75) Inventors: Roghieh Saffie-Siebert, Down (GB); Nasrollah Torabi-Pour, Down (GB)

(73) Assignee: SiSaf Limited, Belfast (GB)

( * ) Notice: Subject to any disclaimer, the term of this patent is extended or adjusted under 35 U.S.C. 154(b) by 0 days.

(21) Appl. No.: 14/234,944

(22) PCT Filed: Jul. 27, 2012

(86) PCT No.: PCT/GB2012/051842
§ 371 (c)(1),
(2), (4) Date: Apr. 25, 2014

(87) PCT Pub. No.: WO2013/014473
PCT Pub. Date: Jan. 31, 2013

(65) Prior Publication Data
US 2014/0308353 A1    Oct. 16, 2014

(30) Foreign Application Priority Data

Jul. 27, 2011   (GB) .................................. 1112950.9

(51) Int. Cl.
| | |
|---|---|
| *A61K 8/02* | (2006.01) |
| *A61K 9/16* | (2006.01) |
| *A61K 8/25* | (2006.01) |
| *A61K 8/67* | (2006.01) |
| *A61K 9/00* | (2006.01) |
| *A61K 31/07* | (2006.01) |
| *A61Q 19/00* | (2006.01) |

(52) U.S. Cl.
CPC .......... *A61K 9/1611* (2013.01); *A61K 8/0279* (2013.01); *A61K 8/25* (2013.01); *A61K 8/671* (2013.01); *A61K 9/0014* (2013.01); *A61K 31/07* (2013.01); *A61Q 19/00* (2013.01); *A61K 2800/56* (2013.01)

(58) Field of Classification Search
CPC ........ A61K 8/25; A61K 8/671; A61K 9/0014; A61K 9/1611; A61K 31/07; A61K 8/0279; A61K 2800/56; A61Q 19/00
See application file for complete search history.

(56) References Cited

U.S. PATENT DOCUMENTS

| | | | |
|---|---|---|---|
| 5,690,945 A * | 11/1997 | Bui-Bertrand et al. | ...... 424/401 |
| 5,955,109 A | 9/1999 | Won et al. | |
| 2003/0108580 A1 * | 6/2003 | Hasenzahl et al. | ........... 424/401 |
| 2008/0260664 A1 | 10/2008 | Walenzyk et al. | |
| 2011/0229540 A1 * | 9/2011 | Canham | .................. A61K 8/25 424/401 |
| 2012/0128786 A1 * | 5/2012 | Saffie-Siebert | ............... 424/600 |

FOREIGN PATENT DOCUMENTS

| | | |
|---|---|---|
| WO | WO-98/51282 A1 | 11/1998 |
| WO | WO-03/105806 A1 | 12/2003 |
| WO | WO-2011/012867 A1 | 2/2011 |

OTHER PUBLICATIONS

Chiappini et al ("Tailored porous silicon microparticles: fabrication and properties," Chemphyschem. Apr. 6, 2010; 11(5): 1029-1035).*
International Preliminary Report on Patentability mailed Feb. 6, 2014 in PCT Application No. PCT/GB2012/051842 (8 pages).
International Search Report mailed Dec. 21, 2012 in PCT Application No. PCT/GB2012/051842 (4 pages).

* cited by examiner

*Primary Examiner* — Suzanne Ziska
(74) *Attorney, Agent, or Firm* — Foley & Lardner LLP; Christopher J. McKenna (57) ABSTRACT

A composition for use as a topical delivery system for an active material is provided, the composition comprising a plurality of skin cell removal particles and a plurality of active material molecules, at least some of the skin cell removal particles each carrying at least one active material molecule, wherein carrying of an active material molecule by a skin cell removal particle maintains activity of the active material molecule. A topical delivery system for an active material, and a method of topical delivery of an active material are also provided.

17 Claims, 3 Drawing Sheets

DELIVERY OF AN ACTIVE MATERIAL

RELATED APPLICATIONS

This application is a U.S. National Stage of International Application Number PCT/GB2012/051842, filed Jul. 27, 2012, which claims the benefit of priority to GB Application Number 1112950.9, filed Jul. 27, 2011. The entire contents of the foregoing are hereby incorporated herein by reference.

FIELD OF THE INVENTION

The invention relates to a system and method for delivery of an active material into skin.

BACKGROUND TO THE INVENTION

The skin of human and other animal bodies comprises the epidermis and dermis. The epidermis is outermost and comprises a number of layers or strata. The epidermis is continually renewed, through production of cells in the innermost stratum, which cells move outwards until the outermost stratum of the epidermis, the stratum corneum, is reached. During this process, the cells die, their contents are substantially replaced by keratin, and their shape changes from substantially spheroid to a more flattened shape. The stratum corneum is therefore made up of dead cells. These are provided in a number of layers, for example 10 to 150 layers. Cells in each layer, because of their flattened shape, can overlap with cells in adjacent layers forming a barrier for the body which has low permeability. The barrier is important for protecting the body from loss of water and the ingress of harmful substances. The barrier, however, also substantially impedes the penetration of beneficial materials placed on the skin and therefore reduces the ability to deliver the materials to deeper layers of the skin and other parts of the body. On their own, beneficial materials often cannot penetrate the barrier of the skin provided by the layers of the stratum corneum quickly and efficiently enough to provide sufficient therapeutic effects.

Various techniques have been developed for mitigating the low permeability of the stratum corneum barrier, to allow therapeutic materials past the barrier using minimally invasive technologies that can penetrate the skin's outermost layers without stimulating the nerves. Such techniques include chemical diffusion enhancers, iontophoretic devices, adhesives, microneedle arrays, and sonophoretic devices. While many of these techniques can be effective, their use can be hampered by side effects and often also require application by professional personnel.

SUMMARY OF THE INVENTION

According to a first aspect of the invention there is provided a composition for use as a topical delivery system for an active material, the composition comprising a plurality of skin cell removal particles and a plurality of active material molecules, at least some of the skin cell removal particles each carrying at least one active material molecule, wherein carrying of an active material molecule by a skin cell removal particle maintains activity of the active material molecule.

In topical active material delivery systems, it is important that the active material is able to get beyond the skin barrier provided by the stratum corneum, and it is important that the material is still active at this point in order for the material to be taken up by the skin. It has been appreciated that these objectives can both be realised by using a composition comprising skin cell removal particles carrying active material molecules. The skin cell removal particles will allow the thickness of the stratum corneum to be reduced, enabling the active material molecules to overcome the skin barrier. The skin cell removal particles also carry the active material molecules maintaining their activity.

Compositions exist which comprise skin cell removal, or exfoliate, particles and active materials. However, in these compositions the active materials are not carried by the exfoliate particles, the active materials and exfoliate particles are merely mixed together. This means that the activity of the active materials will not be maintained, allowing them to become inactive and unable to be taken up by skin. This is especially the case with biological active materials.

Carrying the at least one active material molecule may comprise loading the active material molecule in a pore of a porous skin cell removal particle. Loading the active material molecule may comprise using an incubation method or a lyophilisation method or any other conventional loading method known in the art. The porous skin cell removal particles may be comprised from any of porous silicon, porous crystal, porous germanium, porous diamonds, porous gold, porous ceramic, porous boron. It will be understood that the skin cell removal material is not limited to those listed but may be any porous skin cell removal material as is known in the art.

Carrying the at least one active material molecule may comprise depositing the active material molecule within a shell of a hollow skin cell removal particle.

Carrying the at least one active material molecule may comprise fixing the active material molecule onto an external surface of a skin cell removal particle. Fixing the active material molecule may comprise adsorption of the active material molecule onto the skin cell removal particle.

Carrying the at least one active material molecule may comprise linking the active material molecule to a skin cell removal particle. The active material molecule may be directly linked to the skin cell removal particle. The active material may be directly linked to the skin cell removal particle by any of ionic bonding, covalent bonding, H bonding. The active material molecule may be linked to the skin cell removal particle by a linkage material. The active material molecule may be linked to the skin cell removal particle by a linkage material by any of ionic bonding, covalent bonding, H bonding. The linkage material may comprise any of fatty acids, amino acids, lipids. It will be understood that the linkage material is not limited to those listed but may be any such material as is known in the art.

Carrying the at least one active material molecule may comprise a combination of loading the active material molecule in a pore of a porous skin cell removal particle, depositing the active material molecule within a shell of a hollow skin cell removal particle, fixing the active material molecule onto an external surface of a skin cell removal particle, linking the active material molecule to a skin cell removal particle.

Carrying the at least one active material molecule may comprise carrying a delivery vehicle molecule which, in turn, carries the active material molecule.

Carrying the at least one active material molecule may comprise loading a delivery vehicle molecule carrying the active material molecule in a pore of a porous skin cell removal particle. Loading the delivery vehicle molecule carrying the active material molecule may comprise using an incubation method or a lyophilisation method or any other conventional loading method known in the art. The porous skin cell removal particles may be comprised from any of porous silicon, porous crystal, porous germanium, porous diamonds, porous gold, porous ceramic, porous boron. It will again be understood that the skin cell removal material is not limited to those listed but may be any porous skin cell removal material as is known in the art.

Carrying the at least one active material molecule may comprise depositing a delivery vehicle molecule carrying the active material molecule within a shell of a hollow skin cell removal particle.

Carrying the at least one active material molecule may comprise fixing a delivery vehicle molecule carrying the active material molecule onto an external surface of a skin cell removal particle. Fixing the delivery vehicle molecule carrying the active material molecule may comprise adsorption of the delivery vehicle molecule carrying the active material molecule onto the skin cell removal particle.

Carrying the at least one active material molecule may comprise linking a delivery vehicle molecule carrying the active material molecule to a skin cell removal particle. The delivery vehicle molecule carrying the active material molecule may be directly linked to the skin cell removal particle. The delivery vehicle molecule carrying the active material molecule may be linked to the skin cell removal particle by a linkage material. The linkage material may comprise any of fatty acids, amino acids, lipids. It will again be understood that the linkage material is not limited to those listed but may be any such material as is known in the art.

Carrying the at least one active material molecule may comprise any combination of loading a delivery vehicle molecule carrying the active material molecule in a pore of a porous skin cell removal particle, depositing a delivery vehicle molecule carrying the active material molecule within a shell of a hollow skin cell removal particle, fixing a delivery vehicle molecule carrying the active material molecule onto an external surface of a skin cell removal particle, linking a delivery vehicle molecule carrying the active material molecule to a skin cell removal particle.

The delivery vehicle may comprise a plurality of nanospheres. The nanospheres may have a melting point in the range from about 20° C. to about 100° C., preferably from about 30° C. to about 90° C. The delivery vehicle may comprise any of lipid-based materials, polymer-based materials, liposomes, niosomes, polymers, dendrimers, emulsions, collagen, ceramides, cholesterol, cyclodextrin. It will be understood that the delivery vehicle is not limited to those listed but may be any such vehicle as is known in the art. The delivery vehicle may be used to control release of the active material molecule.

The amount of active material carried by the skin cell removal particles may be in the range of about 0.1% to about 50%. The encapsulation efficiency of active material by the skin cell removal particles may be in the range of about 60% to about 99%.

Carrying of an active material molecule may maintain activity thereof by any of maintaining stability of the active material molecule, e.g. by protecting against degradation or by reducing crystallization, maintaining or improving solubility of the active material molecule, e.g. aqueous or oil solubility, increasing partitioning of the active material molecules.

The skin cell removal particles may comprise granules or beads. The skin cell removal particles may be comprised from inorganic materials or organic materials. The skin cell removal particles may comprise microparticles or nanoparticles. The skin cell removal particles may have a size in the range of about 100 nm to about 1000 nm. The skin cell removal particles may have a superficial charge in the range of about −50 mV to about +50 mV.

The skin cell removal particles may comprise abrasive particles. The skin cell removal particles may comprise chemical peeling particles.

Suitably, the skin cell removal particles content of the composition is within the range of 0.01-50 wt %, preferably within the range of 0.01-10 wt %, more preferably within the range of 0.1-10 wt %, and most preferably within the range of 0.1-5 wt %.

The active material may comprise a hydrophilic material or a hydrophobic material. The active material molecules may be large molecular weight molecules or small molecular weight molecules.

The active material may comprise any of vitamins, moisturizing agents, anti-UV agents, anti-inflammatory agents, anti-oxidants, free radical scavengers, anti-seborrhoeic agents, keratolytic agents, refreshing agents, melanoregulators, liporegulators, anti-ageing agents, anti-bacterial agents, vascular protectors, anti-fungal agents, skin conditioners, immunomodulators, nutrients, essential oils, retinoids, anaesthetics, vaccines, antigens, anti-bodies, alone or in combination. It will be understood that the active material is not limited to those listed but may be any such material as is known in the art.

The composition may comprise a plurality of skin cell removal materials and a plurality of active materials, carried as described above.

According to a second aspect of the invention there is provided a topical delivery system for an active material comprising a composition according to the first aspect of the invention.

The topical delivery system may be formulated in a formulation which is compatible with the composition. The topical delivery system may further comprise a base. The base may be a pharmaceutical base or a cosmetic base. The base may comprise any of a liquid, paste, cream, emulsion, lotion, gel, dispersion, stick, spray, foam, tincture, ointment, polisher, scrub, application device, or the like. The topical delivery system may further comprise a diluent such as any of water, aqueous alcohol, glycol. The topical delivery system may further comprise a material such as any of emollient, moisturiser, emulsifier, neutraliser, colouring agent, ultra violet absorber or filter, preservative, gelling agent.

The topical delivery system may comprise a skin cell removal particles content in the range of from about 1 to 30 wt %, for example from about 2 to 20 wt %, preferably from about 3 to 15 wt %, based on the total weight of the delivery system. The total content of skin cell removal particles is dependent on the active material being delivered and the application in which the delivery system is used. Accordingly, the topical delivery system may be used in a dosing regimen which is suitable for most pharmaceutical and cosmetic utilities.

The topical delivery system may comprise a composition comprising skin cell removal particles linked to a linkage material linked to a delivery vehicle carrying active material molecules. The topical delivery system may comprise on a weight basis: from about 1% to about 20% of the skin cell removal particles, from about 1% to about 10% of the linkage material, from about 1% to about 20% of the delivery vehicle, from about 0.01% to about 20% of the active material molecules and from about 50% to about 80% additional material such as any of thickening agent, diluent, paste, fragrance, solvent, water, preservative or a mixture thereof.

According to a third aspect of the invention there is provided a method of topical delivery of an active material comprising applying a delivery system for the active material according to the second aspect of the invention to a portion of skin, dissociation of skin cell removal particles and active material molecules of the delivery system, working the delivery system against the portion of skin to remove stratum corneum cells therefrom, thereby allowing dissociated active material molecules to reach sub corneum skin layers.

The delivery system may be applied manually to the skin. The delivery system may be applied to the skin using an application device.

Dissociation of skin cell removal particles and active material molecules may occur on the skin surface by partitioning of the active material molecules between the skin and the skin cell removal particles.

Working the delivery system against the skin may remove substantially all layers of stratum corneum cells of the skin portion providing a gap which allows the active material molecules to reach sub corneum skin layers.

Working the delivery system against the skin may remove some layers of stratum corneum cells of the skin portion which allows the active material molecules to penetrate through remaining layers of stratum corneum cells of the skin portion to sub corneum skin layers. Working the delivery system against the skin to remove some layers of stratum corneum cells of the skin portion may decrease the packing density of the remaining layers of stratum corneum cells enabling pores of the skin to increase in diameter and allowing the active material molecules to penetrate through the remaining layers of stratum corneum cells by transport thereof through the pores. Working the delivery system against the skin to remove some layers of stratum corneum cells of the skin portion may decrease the packing density of the remaining layers of stratum corneum cells causing spacing of the cells and allowing the active material molecules to penetrate through the remaining layers of stratum corneum cells by penetration between the cells.

Allowing the active material molecules to reach sub corneum skin layers may enable uptake of the active material in the epidermis of the skin. Allowing the active material molecules to reach sub corneum skin layers may enable the active material molecules to travel to the dermis and uptake of the active material in the dermis of the skin. Thus an active material delivery system is provided for the skin.

Allowing the active material molecules to reach sub corneum skin layers may enable the active material molecules to diffuse through the epidermis into the dermis and uptake of the active material in blood vessels and lymphatics of the dermis for delivery of the active material throughout the body. Thus a transdermal active material delivery system is provided for the body.

Using the delivery system and method described above, the active material is able to penetrate to deeper layers of the skin without requiring any chemical or other aggressive skin permeation enhancers. The delivery system and method of the invention offer an enhanced active material delivery system, in terms of enhanced efficiency and efficacy of the active material, for skin care, cosmetic and therapeutic applications, and opens new opportunities for the development of novel improved therapies.

DETAILED DESCRIPTION OF THE INVENTION

Embodiments of the invention will now be described by way of example only, with reference to the accompanying drawings, in which:

FIG. 1 is a schematic representation of manufacture of a first embodiment of a composition according to the first aspect of the invention;

FIG. 2 is a schematic representation of manufacture of a second embodiment of a composition according to the first aspect of the invention, and FIG. 3 is a schematic representation of use of the composition of FIG. 1 in a topical delivery system according to the second aspect of the invention.

Referring to FIG. 1, manufacture of a composition comprising porous silicon skin cell removal particles and vitamin A active material molecules is shown. A silicon wafer (having a silicon dioxide outer shell) is cleaned by the standard known process of soaking the wafer in a solution of HF (28%) and ethanol in a ratio of 3:1 for 10 min. This removes the silicon dioxide outer shell and forms a hydrogen-terminated porous silicon film. The film is fractured into multi-sized hydrogen-terminated porous silicon particles by sonicating in deionised water overnight. The porous silicon particles are filtered using a 0.45 μm filtration membrane (Millipore). A 500 μl solution of porous silicon particles in deionised water is added to 500 μl of 0.1 mg/ml of vitamin A in PBS (pH 9) and incubated overnight at 37° C. (pH 7.0). Each porous silicon particle comprises a plurality of pores and molecules of vitamin A are loaded into one or more of the pores, to form a composition of porous silicon skin cell removal particles which each carry a plurality of vitamin A active material molecules. The surface morphology and roughness of the porous silicon skin cell removal particles and vitamin A active material molecules were characterized by atomic force microscopy.

Referring to FIG. 2, manufacture of a composition comprising silicon skin cell removal particles and emulsion delivery vehicle molecules carrying active material molecules is shown. Approximately 25 mg of silicon particles is placed in a 100 ml beaker and immersed in 10 ml of 10% NaOH, 5 ml of glycerol and neutralised with HCl conc until the pH reaches approximately 7.4 to form silicon particles with surface bound hydroxide groups. The particles are then rinsed with hexane and ethanol to remove excess acid. The emulsion delivery vehicle is composed of 15% (w/w) snake oil, soybean lecithin at a concentration of 7.5% (w/w) and an aqueous glycerol solution with a glycerol concentration of 75% (w/w). Soybean lecithin is dissolved into the snake oil at 50° C. The oil phase is then stirred in the aqueous glycerol solution at 350 rpm and 50° C. for about 10 min. The mixture is emulsified using a stirrer at 1200 rpm for 2 min. Subsequently, active material molecules of vitamin A are added to the delivery vehicle mixture and homogenised, allowing emulsion delivery vehicle molecules to carry vitamin A active material molecules. (Samples may be stored at 25° C. for later use.) Approximately 4 mg of the silicon particles with surface bound hydroxide groups are then suspended in 500 ml of ethanol. Next, the vehicle delivery emulsion carrying the vitamin A active material molecules and 25 μl of a 10 mg/ml solution of EDAC (commercial grade, Sigma-Aldrich Chemicals) are added. The solution is then agitated for 2 hours at room temperature, allowing surface linkage of the delivery vehicle emulsion to the silicon skin cell removal particles to form a composition of silicon skin cell removal particles which each carry a plurality of delivery vehicle emulsion molecules carrying vitamin A active material molecules. The resultant composition is rinsed thoroughly with PBS. It will be appreciated that the silicon skin cell removal particles may be porous, and the delivery vehicle emulsion molecules carrying the vitamin A active material molecules may also be carried by the silicon skin cell removal particles by deposition of the delivery vehicle emulsion molecules and vitamin A active material molecules in pores of the porous silicon skin cell removal particles.

Figure 1:
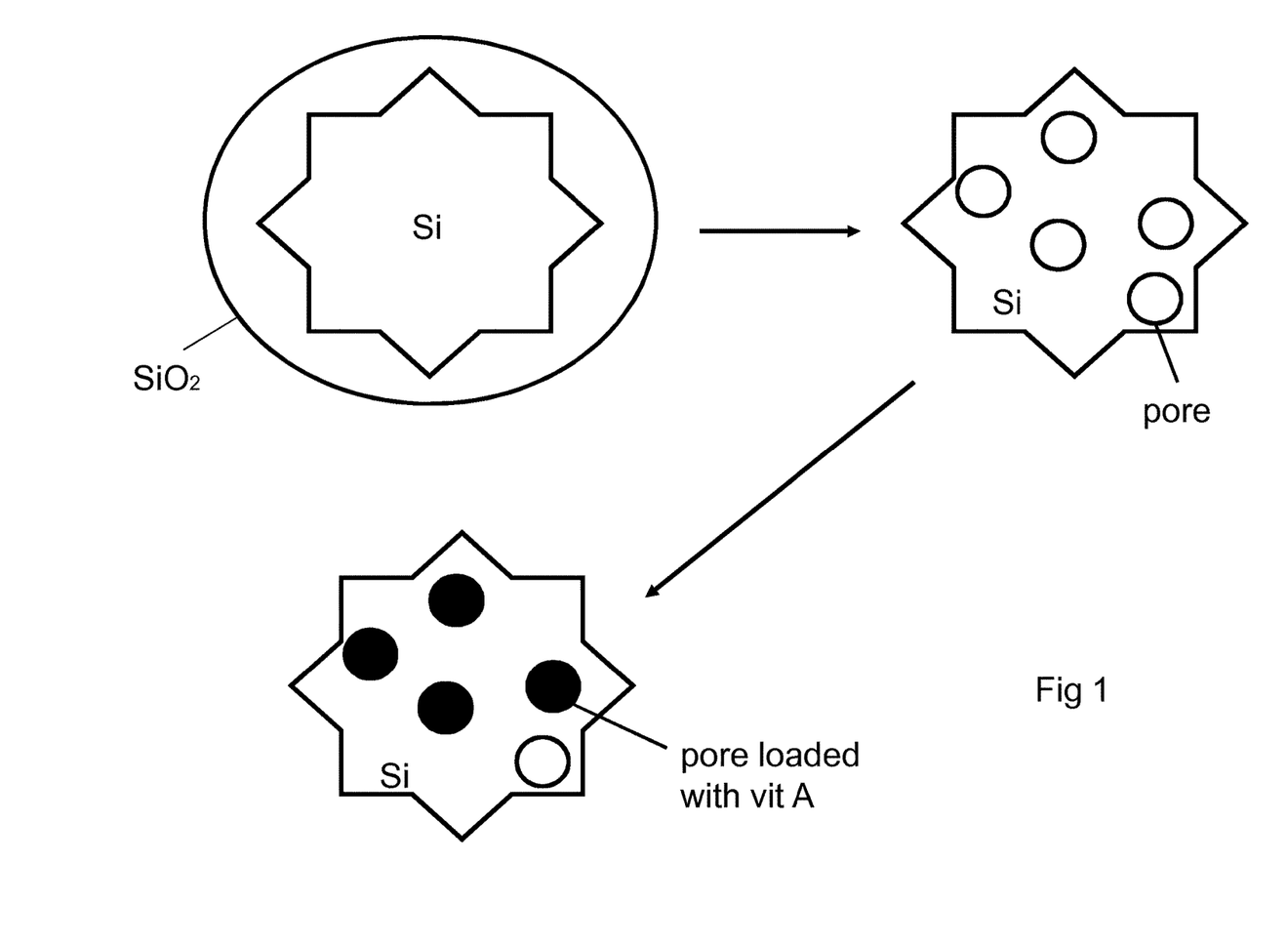
Figure 2:
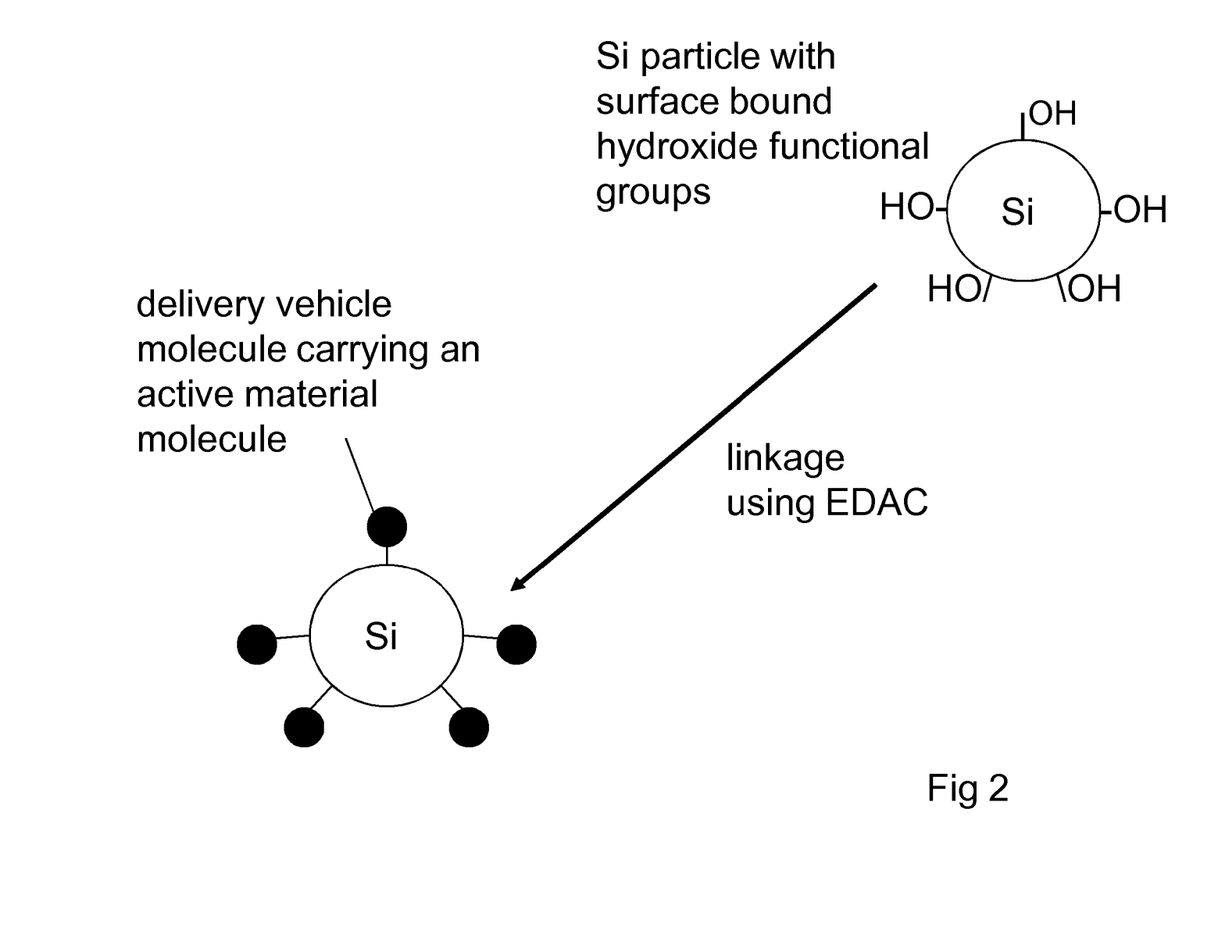
Figure 3:
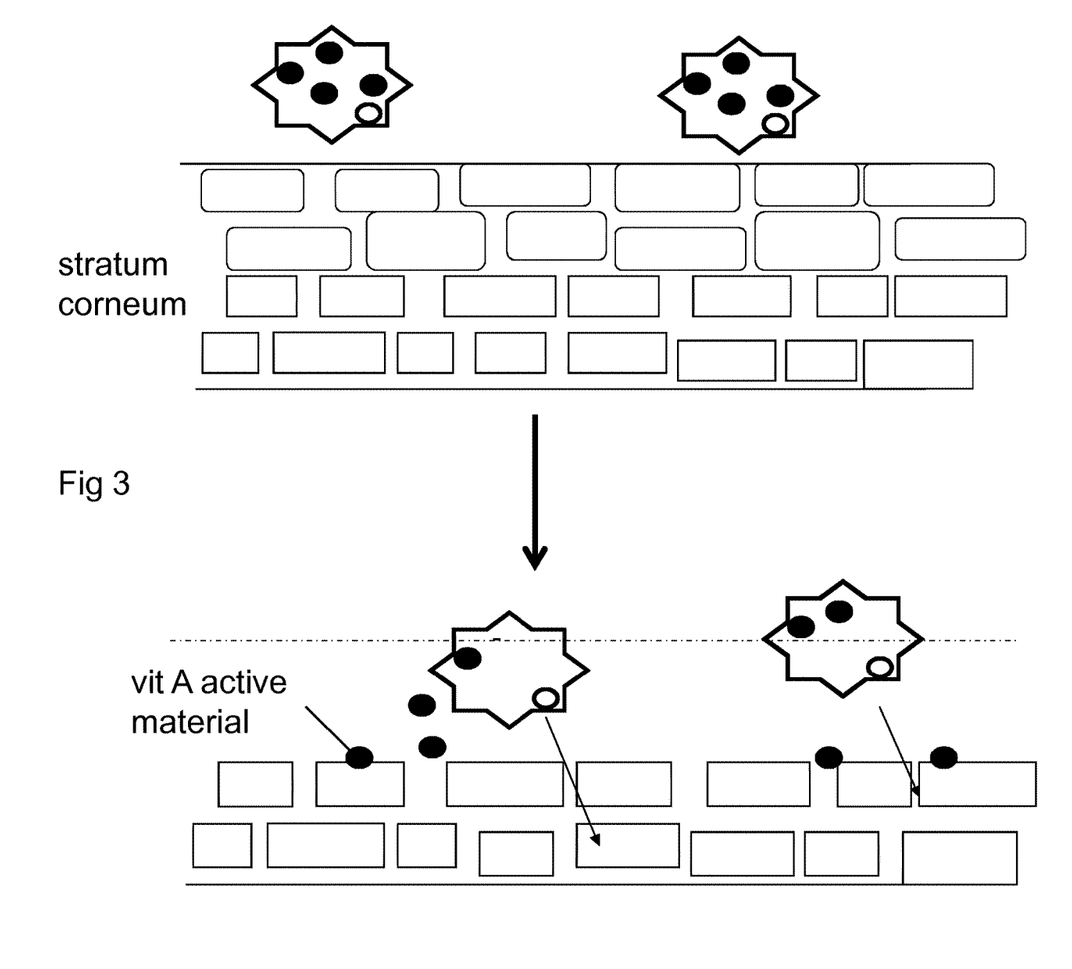

FIG. 3 is a schematic representation of use of the composition of FIG. 1 in a topical delivery system. The topical delivery system is formed from the composition and a base, in this embodiment a lotion. The delivery system is applied to a portion of skin, as shown, and worked against the portion of skin. This allows edges of the porous silicon skin cell removal particles of the composition to remove layers of stratum corneum cells from the portion of the skin. The silicon skin cell removal particles and the vitamin A active material molecules of the composition also dissociate. As some layers of the stratum corneum cells of the skin portion are removed, this allows the vitamin A active material molecules to penetrate through remaining layers of stratum corneum cells of the skin portion to sub corneum skin layers, as shown. Working the delivery system against the skin to remove some layers of stratum corneum cells of the skin portion decreases the packing density of the remaining layers of stratum corneum cells enabling pores of the skin to increase in diameter and allowing the active material molecules to penetrate through the remaining layers of stratum corneum cells by transport thereof through the pores. Decreasing the packing density of the remaining layers of stratum corneum cells also causes spacing of the cells, allowing the vitamin A active material molecules to penetrate through the remaining layers of stratum corneum cells by penetration between the cells.

Referring to Table 1, an investigation of recovery of active material molecules from various compositions will be discussed. The active material molecules are carried by a plurality of skin cell removal particles, which maintains the stability of the active material molecules, the greater the amount of the active material molecules recovered from a composition, the greater the stability of the molecules. The active material molecules comprise Vitamin A, and the skin cell removal particles comprise silicon particles (Si—P) (which may be nanoparticles and/or micron-sized particles), particles of ABRASIL®, and a combination of silicon particles and particles of ABRASIL®. The various compositions further comprise either a cream or a solution.

The results of the investigation were compared to results of recovery of the active material molecules from compositions which do not comprise skin cell removal particles. Two compositions, F and K, were prepared comprising F (cream, 0.05% vitamin A) and K (solution, 0.05% vitamin A). Referring to Table 1, it can be seen that vitamin A, either in solution or when formulated in cream, has low stability. The starting value of 82.8% recovery in F (cream, vit A) is reduced to 64.55% after 48 h at room temperature (RT), 20-24° C. The starting value of nominal 100% of vitamin A in K (solution, vit A) is reduced to 66.97% after 48 h at RT. Vitamin A in F (cream, vit A) and in K (solution, vit A) show similar stability at the 48 h test point, with a recovery value of 64.55% for F (cream, vit A) compared to 66.97% for K (solution, vit A).

TABLE 1

| | | Vitamin A recovered Time (hour) | | | | | | | |
|---|---|---|---|---|---|---|---|---|---|
| Samples | Methods | 0 mg | 0 % | 1 mg | 1 % | 3 mg | 3 % | 6 mg | 6 % |
| A cream | D | NA | NA | 0.08 | 3.25 | 0.22 | 9.06 | 0.40 | 16.0 |
| | E | 2.08 | 83.4 | 2.05 | 79.2 | 1.91 | 76.6 | 1.76 | 70.6 |
| vit A Si—P ABRASIL ® | Total % | | 83.4 | | 82.5 | | 85.7 | | 86.6 |
| C cream | D | NA | NA | 0.09 | 3.48 | 0.21 | 8.6 | 0.38 | 15.5 |
| | E | 2.04 | 81.9 | 2.04 | 79.0 | 1.86 | 74.6 | 1.72 | 68.8 |
| vit A Si—P | Total % | | 81.9 | | 82.5 | | 83.2 | | 84.3 |
| D cream | D | NA | NA | 0.03 | 1.39 | 0.08 | 3.48 | 0.21 | 8.6 |
| | E | 2.08 | 83.2 | 2.09 | 80.7 | 1.99 | 79.8 | 1.87 | 75.1 |
| vit A ABRASIL ® | Total % | | 83.2 | | 82.1 | | 83.2 | | 83.7 |
| F cream | D | NA | NA | 0.03 | 1.16 | 0.05 | 2.09 | 0.12 | 4.88 |
| | E | 2.07 | 82.8 | 2.04 | 79.0 | 1.93 | 77.5 | 1.83 | 73.3 |
| vit A | Total % | | 82.8 | | 80.2 | | 79.6 | | 78.1 |
| Control solutions | | | | | | | | | |
| G solution | D | NA | | 0.09 | 2.32 | 0.27 | 10.8 | 0.39 | 15.6 |
| | E | NA | | | NA | | NA | | NA |
| vit A Si—P ABRASIL ® | Total % | | | 2.08 | 83.37 | 1.98 | 79.5 | 2.00 | 80.2 |
| H solution | D | NA | | 0.02 | 0.69 | 0.2 | 8.37 | 0.31 | 12.5 |
| | E | NA | | | NA | | NA | | NA |
| vit A ABRASIL ® | Total % | | | 2.05 | 82.32 | 1.96 | 78.4 | 1.98 | 79.5 |

TABLE 1-continued

|  |  | Vitamin A recovered Time (hour) | | | | | | |
|---|---|---|---|---|---|---|---|---|
| J solution | D<br>E | NA<br>NA | 0.09<br>NA | 2.55 | 0.25<br>NA | 10.1 | 0.44<br>NA | 17.7<br>NA |
| vit A Si—P | Total % |  | 2.07 | 83.02 | 2.05 | 82.3 | 2.06 | 82.6 |
| K solution | D<br>E | NA<br>NA | 0.009<br>NA | 0.23 | 0.06<br>NA | 2.44 | 0.07<br>NA | 3.13<br>NA |
| vit A | Total % |  | 2.06 | 82.67 | 2.040 | 81.6 | 2.005 | 80.2 |

| Samples | Methods | 14 | | 24 | | 48 | |
|---|---|---|---|---|---|---|---|
|  |  | mg | % | mg | % | mg | % |
| A cream | D<br>E | 0.88<br>1.25 | 35.3<br>50.23 | 1.24<br>0.88 | 49.7<br>35.3 | 1.49<br>0.62 | 59.77<br>25.11 |
| vit A Si—P ABRASIL® | Total % |  | 85.53 |  | 85.0 |  | 84.88 |
| C cream | D<br>E | 0.83<br>1.20 | 33.2<br>48.37 | 1.25<br>0.73 | 50.2<br>29.3 | 1.43<br>0.54 | 57.2<br>21.76 |
| vit A Si—P | Total % |  | 81.57 |  | 79.5 |  | 78.96 |
| D cream | D<br>E | 0.34<br>1.72 | 13.95<br>68.83 | 0.52<br>1.53 | 20.9<br>61.3 | 0.58<br>1.39 | 23.25<br>55.81 |
| vit A ABRASIL® | Total % |  | 82.78 |  | 82.3 |  | 79.06 |
| F cream | D<br>E | 0.20<br>1.69 | 8.13<br>67.72 | 0.35<br>1.49 | 14.1<br>59.7 | 0.30<br>1.31 | 12.09<br>52.46 |
| vit A | Total % |  | 75.85 |  | 73.9 |  | 64.55 |
|  |  | Control solutions | | | | | |
| G solution | D<br>E | 0.87<br>NA | 34.8<br>NA | 1.05<br>NA | 42.2<br>NA | 1.09<br>NA | 43.6<br>NA |
| vit A Si—P ABRASIL® | Total % | 2.06 | 82.6 | 2.04 | 81.6 | 1.91 | 76.74 |
| H solution | D<br>E | 0.78<br>NA | 31.3<br>NA | 0.95<br>NA | 38.3<br>NA | 0.69<br>NA | 27.9<br>NA |
| vit A ABRASIL® | Total % | 1.94 | 77.7 | 1.91 | 76.7 | 1.87 | 75 |
| J solution | D<br>E | 0.82<br>NA | 33.1<br>NA | 0.99<br>NA | 39.7<br>NA | 1.05<br>NA | 42.2<br>NA |
| vit A Si—P | Total % | 2.04 | 81.6 | 1.98 | 79.5 | 1.93 | 77.44 |
| K solution | D<br>E | 0.08<br>NA | 3.48<br>NA | 0.10<br>NA | 4.18<br>NA | 0.09<br>NA | 3.83<br>NA |
| vit A | Total % | 1.94 | 77.7 | 1.91 | 76.7 | 1.67 | 66.97 |

D: dialysis,
E: extraction

Two compositions, C and J, were prepared comprising C (cream, 0.05% vitamin A, 0.1% Si—P) and J (solution, 0.05% vitamin A, 0.1% Si—P). At least some of the silicon particles are porous and at least some of the silicon particles are non porous. Vitamin A molecules are carried by the silicon particles by both loading of vitamin A molecules in pores of the silicon particles and by fixing of vitamin A molecules to an external surface of the silicon particles. Referring to Table 1, it can be seen that carrying of vitamin A molecules by silicon particles results in increased stability of the vitamin A both in C (cream, vit A, Si—P), 78.96% vitamin A recovery after 48 h at RT compared to 64.55% vitamin A recovery for F (cream, vit A), and in J (solution, vit A, Si—P), 77.44% recovery after 48 h at RT compared to 66.97% recovery for K (solution, vit A). Formulating vitamin A-loaded silicon particles in a cream, shows comparable stability to vitamin A-loaded silicon particles in solution, 78.96% vitamin A recovery from C (cream, vit A, Si—P) after 48 h at RT, and 77.44% recovery of vitamin A from J (solution, vit A, Si—P) after 48 h at RT. Loading of vitamin A in pores of silicon particles results in significantly larger quantities of vitamin A being released in the dialysis medium, 42.2% release of vitamin A-loaded silicon particles for J (solution, vit A, Si—P) after 48 h at RT compared to 3.83% release of vitamin A for K (solution, vit A) after 48 h at RT. Loading of vitamin A in silicon particles has changed the properties of the vitamin A and enhanced diffusion of this highly hydrophobic active material through cellulose acetate dialysis membrane, 57.2% release of vitamin A-loaded silicon particles for C (cream, vit A, Si—P) at 48 h compared to 12.09% release of vitamin A for F (cream, vit A) at 48 h. The results of total recovery of vitamin A in Table 1 for C (cream, vit A, Si—P) and J (solution, vit A, Si—P) clearly demonstrate that using silicon particle skin cell removal particles to carry vitamin A active material molecules improves the stability, and hence the activity, of the vitamin A active material molecules.

Two compositions, D and H, were prepared comprising D (cream, 0.05% vitamin A, 1% ABRASIL®) and H (solution, 0.05% vitamin A, 1% ABRASIL®). ABRASIL® provides skin cell removal particles and partly comprises porous clay and partly comprises silicon. Vitamin A active material molecules are carried by the ABRASIL® by both loading of vitamin A molecules in pores of the ABRASIL® porous clay, using a standard method such as dehydration-rehydration or a homogenizer method, and by linking of vitamin A molecules to ABRASIL® particles, by charge-charge interaction. Referring to Table 1, it can be seen that carrying of vitamin A active material molecules by ABRASIL® skin cell removal particles results in increased stability of the vitamin A both in H (solution, vit A, ABRASIL®), 75% vitamin A recovery after 48 h at RT compared to 66.97% vitamin A recovery for K (solution, vit A), and in D (cream, vit A, ABRASIL®), 79.06% vitamin A recovery after 48 h at RT compared to 64.55% vitamin A recovery for F (cream, vit A). The results of recovery of vitamin A in Table 1 for D (cream, vit A, ABRASIL®) and H (solution, vit A, ABRASIL®) clearly demonstrate that using ABRASIL® skin cell removal particles to carry vitamin A active material molecules improves the stability, and hence the activity, of the vitamin A active material molecules.

Two further compositions, A and G, were prepared comprising A (cream, 0.05% vitamin A, 0.1% Si—P, 1% ABRASIL®) and G (solution, 0.05% vitamin A, 0.1% Si—P, 1% ABRASIL®). At least some of the silicon particles are porous and at least some of the silicon particles are non porous. Vitamin A molecules are carried by the silicon particles by both loading of vitamin A molecules in pores of the silicon particles and by fixing of vitamin A molecules to an external surface of the silicon particles. Vitamin A active material molecules are also carried by the ABRASIL® particles by both loading of vitamin A molecules in pores of the ABRASIL® porous clay and by linking of vitamin A molecules to ABRASIL® particles. Referring to Table 1, it can be seen that combining carrying of vitamin A active material molecules by silicon particles and ABRASIL® particles gives the best results in total recovery (and therefore stability and activity) of vitamin A from the cream formulations, see vitamin A recovery of 84.88% at 48 h from A (cream, vit A, Si—P, ABRASIL®). However, inclusion of ABRASIL® in cream formulation containing vitamin A loaded silicon particles has no significant effect on the rate or extent of vitamin A release or recovery, and hence stability, in the first 48 h of testing. Loading of vitamin A in pores of silicon particles resulted in significantly larger quantities of vitamin A being released in the dialysis medium. Addition of ABRASIL® to vitamin A-loaded silicon particles has no significant effect on this release rate of vitamin A, with a value of 43.6% release of vitamin A from G (solution, vit A, Si—P, ABRASIL®) at 48 h compared to 42.2% release of vitamin A from J (solution, vit A, Si—P) at 48 h. Carrying of vitamin A by silicon particles changed the properties of vitamin A and enhanced diffusion of this highly hydrophobic active material through cellulose acetate dialysis membrane. Addition of ABRASIL® does not demonstrate an additional enhancing effect, 59.77% vitamin A release at 48 h for A (cream, vit A, Si—P, ABRASIL®) compared to 57.2% vitamin A release for C (cream, vit A, SiP) at 48 h.

It will be understood by those skilled in the art that various modifications may be made in the present invention without departing from the spirit and scope thereof, as described in the specification and defined in the appended claims.

The invention claimed is:

1. A composition comprising a plurality of skin cell removal particles and a plurality of active material molecules,
   wherein the skin removal particles comprise at least one elemental silicon particle,
   wherein the elemental silicon particle has a jagged outer surface,
   wherein at least some of the skin cell removal particles each carry at least one active material molecule, and
   wherein carrying of at least one active material molecule by a skin cell removal particle stabilizes an activity of the at least one active material molecule.

2. The composition of claim 1, wherein at least some of the skin cell removal particles comprise one or more pores, wherein at least one active material molecule is disposed in at least some of the pores.

3. The composition of claim 1, wherein at least some of the skin cell removal particles comprise a hollow shell, wherein at least one active material molecule is disposed in at least some of the hollow shells.

4. The composition of claim 1, wherein the at least one active material molecule is detachably fixed onto an external surface of a skin cell removal particle.

5. The composition of claim 1, wherein the at least one active material molecule is detachably linked to a skin cell removal particle.

6. The composition of claim 1, wherein the at least one active material molecule is carried by a delivery vehicle molecule, and wherein at least one delivery vehicle molecule is carried by a skin cell removal particle.

7. The composition of claim 6, wherein the delivery vehicle is one or more delivery vehicles selected from the group consisting of lipid-based materials, polymer-based materials, liposomes, niosomes, polymers, dendrimers, emulsions, collagen, ceramides, cholesterol and cyclodextrin.

8. The composition of claim 1, wherein the carrying of at least one active material molecule by a skin cell removal particle maintains one or more activities of the active material molecule selected from the group consisting of maintaining stability of the active material molecule, maintaining solubility of the active material molecule, improving solubility of the active material molecule, and increasing partitioning of the active material molecules.

9. The composition of claim 1, wherein the active material molecule is one or more molecules selected from the group consisting of vitamins, moisturizing agents, anti-UV agents, anti-inflammatory agents, anti-oxidants, free radical scavengers, anti-seborrhoeic agents, keratolytic agents, refreshing agents, melanoregulators, liporegulators, anti-ageing agents, anti-bacterial agents, vascular protectors, anti-fungal agents, skin conditioners, immunomodulators, nutrients, essential oils, retinoids, anaesthetics, vaccines, antigens and anti-bodies.

10. A topical delivery system for an active material comprising a composition according to claim 1.

11. A method for topical delivery of an active material comprising
applying a composition to a portion of skin, wherein the composition comprises a plurality of skin cell removal particles and a plurality of active material molecules, wherein at least some of the skin cell removal particles each carry at least one active material molecule,
wherein carrying of at least one active material molecule by a skin cell removal particle maintains activity of the at least one active material molecule;
working the composition against the portion of skin to remove stratum corneum cells;
dissociating the active material molecules from the skin cell removal particles; and
delivering the active material molecules to sub-corneum skin layers.

12. The method of claim 11, wherein working the composition against the skin removes substantially all stratum corneum cells of the skin portion providing a gap which allows the active material molecules to reach sub-corneum skin layers.

13. The method of claim 11, wherein working the composition against the skin removes some layers of stratum corneum cells of the skin portion which allows the active material molecules to penetrate through remaining layers of stratum corneum cells of skin portion to sub-corneum skin layers.

14. The method of claim 11, wherein working the composition against the skin to remove some layers of stratum corneum cells of the skin portion decreases the packing density of the remaining layers of stratum corneum cells enabling pores of the skin to increase in diameter and allowing the active material molecules to penetrate through the remaining layers of stratum corneum cells by transport thereof through the pores.

15. The method of claim 11, wherein working the composition against the skin to remove some layers of stratum corneum cells of the skin portion decreases the packing density of the remaining layers of stratum corneum cells causing spacing of the cells and allowing the active material molecules to penetrate through the remaining layers of stratum corneum cells by penetration between the cells.

16. The composition of claim 1, wherein the skin cell removal particles further comprises one or more particles selected from the group consisting of porous silicon, porous crystal, porous germanium, porous diamond, porous gold, porous ceramic, and porous boron.

17. The composition of claim 1, wherein the skin cell removal particles comprise about 0.01 to 50 wt % of the composition.

* * * * *